US008111851B2

(12) United States Patent
Giesner et al.

(10) Patent No.: US 8,111,851 B2
(45) Date of Patent: Feb. 7, 2012

(54) HEARING AID WITH ADAPTIVE START VALUES FOR APPARATUS

(75) Inventors: Arthur Giesner, Erlangen (DE); Volkmar Hamacher, Neunkirchen am Brand (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 1320 days.

(21) Appl. No.: 11/729,758

(22) Filed: Mar. 29, 2007

(65) Prior Publication Data

US 2007/0230726 A1 Oct. 4, 2007

(30) Foreign Application Priority Data

Mar. 31, 2006 (DE) ......................... 10 2006 015 450

(51) Int. Cl.
*H04R 25/00* (2006.01)
*H04R 29/00* (2006.01)
*A61N 1/00* (2006.01)

(52) U.S. Cl. ............... 381/321; 381/60; 381/56; 607/56

(58) Field of Classification Search .................... 381/60, 381/312, 320, 321, 106, 107, 56, 57; 600/25; 607/56–57
See application file for complete search history.

(56) References Cited

U.S. PATENT DOCUMENTS 4,972,487 A 11/1990 Mangold
5,604,812 A 2/1997 Meyer
2003/0072465 A1* 4/2003 Fischer et al. ................ 381/317
2003/0091197 A1* 5/2003 Roeck et al. .................... 381/60
2004/0066944 A1 4/2004 Leenen et al.
2005/0129262 A1 6/2005 Dillon et al.
2006/0083386 A1* 4/2006 Allegro-Baumann et al. . 381/60
2006/0215860 A1 9/2006 Wyrsch
2007/0068728 A1* 3/2007 Steinbuss ...................... 181/104
2007/0147624 A1* 6/2007 Fischer ........................ 381/23.1

FOREIGN PATENT DOCUMENTS

EP 0335542 A2 10/1989
EP 1367857 A1 12/2003
WO WO 2004/056154 A2 7/2004

OTHER PUBLICATIONS

Jenstad et al., "Hearing Aid Troubleshooting Based on Patients' Description", National Centre for Audiology, School of Communication Sciences and Disorders, U of Washington, Seattle, WA, presented at the American Academy of Audiology Conference, Miami Beach, May 1999, American Academy of Audiology Conference, Chicago, IL 2009/.

* cited by examiner

*Primary Examiner* — Curtis Kuntz
*Assistant Examiner* — Jesse Elbin

(57) ABSTRACT

Fine customization of a hearing aid to the individual hearing environments and habits of a user are to be simplified and improved. To this end, when the hearing aid is turned on or when the hearing aid is switched to a particular operating mode, neither the value most recently valid for the parameter prior to turning off or switching to a different operating mode nor the parameter value transferred to the hearing aid at the beginning of programming is set. Rather, from the changes to the value of the parameter taking place during operation of the hearing aid a new start value is ascertained and stored, which value is then set automatically after turning on or switching mode.

18 Claims, 1 Drawing Sheet

HEARING AID WITH ADAPTIVE START VALUES FOR APPARATUS

CROSS REFERENCE TO RELATED APPLICATIONS

This application claims priority of German application No. 10 2006 015 450.9 filed Mar. 31, 2006, which is incorporated by reference herein in its entirety.

FIELD OF THE INVENTION

The invention relates to a method for operating a hearing aid which can be worn on or in the ear of a hearing aid wearer, and also a hearing aid which can be worn on or in the ear of a hearing aid wearer.

BACKGROUND OF THE INVENTION

In the case of a hearing aid, an input signal is received by means of an input converter and converted into an electrical input signal. Normally, at least one microphone which receives an acoustic input signal serves as the input converter. Modern hearing aids frequently comprise a microphone system having a plurality of microphones in order to achieve a reception which is dependent on the angle of incidence of acoustic signals, a directional characteristic. The input converters can however also include a telephone coil or an antenna for receiving electromagnetic input signals. The input signals converted into electrical input signals by the input converter are delivered to a signal processing unit for further processing and amplification. The further processing and amplification takes place in order to compensate for the individual hearing loss of a hearing aid wearer, depending on the signal frequency as a rule. The signal processing unit provides an electrical output signal which is delivered by way of an output converter to the ear of the hearing aid wearer, such that the latter perceives the output signal as an acoustic signal. Earpieces which generate an acoustic output signal are normally used as the output converter. However, output converters for generating mechanical oscillations are also known which directly excite certain parts of the ear, such as the auditory ossicles for example, to cause them to oscillate. Furthermore, output converters are known which directly stimulate nerve cells of the ear.

With regard to hearing aids, parameters affecting the signal processing can usually be set by the hearing aid wearer. One parameter of this type is for example the volume setting. In the case of modern hearing aids, the selected values for the relevant parameters are normally stored in digital form in a memory. In this situation, the setting is made by the user either by using control elements situated directly on the hearing aid or by means of a remote control facility for the hearing aid in question. In addition, parameters can also be selected automatically as a result of a signal analysis, for example as a result of analyzing the acoustic input signal in order to determine the hearing situation in which the hearing aid presently finds itself. Such types of hearing situations are for example "quiet environment", "conversation in background noise", "journey in car", etc.

The central constructional element of the signal processing unit of a modern hearing aid is a digital signal processor (DSP). This can be implemented in a freely programmable, hardwired or hybrid form. The values of selectable parameters which influence the signal processing must first be read from the memory after turning on and transferred into the digital signal processor.

During the customization of a hearing aid to the individual hearing loss of a hearing aid wearer, default settings for the parameters which can be set by the hearing aid wearer are also defined in addition to parameters which the hearing aid wearer is no longer able to change during normal operation of the hearing aid. Also defined is the hearing program in which the hearing aid is operated as standard after being turned on. The default settings defined once in this manner for the respective hearing aid wearer are then set automatically each time after the hearing aid is turned on, in other words read out from a non-volatile memory and transferred into the digital signal processor.

One of the most frequent problems for hearing aid wearers is an incorrect volume setting of the hearing aid for their specific everyday hearing situations. The main reason for this is the fact that the hearing aid is adjusted by the acoustician in artificial hearing situations which generally differ in respect of sound types and levels from the relevant individual hearing situations. This can be corrected by means of volume controls which can be arranged directly on the hearing aid or a remote control facility. However, in the case of digital hearing aids having continuous controls for setting the parameter or parameters the corrected settings lose their current value after the hearing aid is turned off, and when the hearing aid is turned on again are set to the initial value selected during the customization process. If this latter value differs from the preferred value, then it must be adjusted. This requires a further visit to the acoustician and is therefore bothersome for the hearing aid wearer. In addition, the latter must take note of the corresponding correction settings, which is problematical, particularly in the situation when in the case of a hearing aid having a plurality of hearing programs different settings for a particular parameter are offered in different hearing programs in order to customize the signal processing to different hearing situations.

A programmable hearing aid is known from patent specification U.S. Pat. No. 5,604,812, which can be automatically adapted to different hearing environments. For continuous, automatic and autonomous adaptation of its transmission characteristics, the hearing aid includes in addition to a microphone, earphone and amplifier/transmission circuit, a first data memory in which audiometric data is stored, a second data memory in which hearing aid characteristics are stored, a third data memory in which algorithms are stored, a signal analysis unit that determines control signals dependent on input quantities characteristic of the current ambient situation, and also includes a data processing unit, the data processing unit offering hearing aid setting data for the amplifier/transmission circuit from the data of the data memories and from the control signals of the signal analysis unit, so that the transmission characteristics of the amplifier/transmission circuit can be automatically determined from the edited audiometric data, hearing aid characteristics, prescribable algorithms and the input quantities characteristic of the current ambient situation.

A hearing aid with the facility for data recording is known from the publication EP 0 335 542 A2. The recorded data comprises information relating to the frequency with which a switchover between individual hearing programs occurs, and the period of time for which the individual hearing programs are switched to active. The recorded data is read out by a hearing aid acoustician, evaluated and used for renewing settings for the hearing programs.

A method for selecting a suitable hearing program in the case of a multi-program hearing aid is known from the publication WO 2004/056154 A2. In this situation, the selection of a suitable hearing program can also take place by taking account of manual user inputs. For example, the volume setting associated with a hearing program is incremented by one dB each time the user manually increments the volume by any value during operation of this hearing program.

A programmable hearing aid with trainable automatic adaptation to different hearing situations is disclosed in publication US 2005/0129262 A1. In this situation, an automatic customization of the parameter sets available for different hearing situations can take place in a particular mode of operation. The customization takes place depending on the frequency of the changes made manually by a user for a particular parameter.

SUMMARY OF THE INVENTION

The object of the present invention is to simplify and to improve the fine customization of a hearing aid to the individual hearing environments of a user.

This object is achieved by a method for operating a hearing aid which can be worn on or in the ear of a hearing aid wearer and a hearing aid which can be worn on or in the ear of a hearing aid wearer according to the claims.

The hearing aid comprises an input converter for reception of an input signal and conversion into an electrical input signal, a signal processing unit for processing and amplifying the electrical input signal, an output converter for converting the processed and amplified electrical input signal into an output signal which can be perceived by the hearing aid wearer as an acoustic signal, and a memory facility for storing at least one value for a parameter influencing the signal processing as a start value in the turned-off hearing aid, whereby the value of the parameter in the case of the turned-on hearing aid can be set by means of an operating facility which can be actuated by a user or automatically by means of a signal analysis and control unit present in the hearing aid.

After the hearing aid has been turned on or after the hearing aid has been switched from a first operating mode (first hearing program, for example) to a second operating mode (second hearing program, for example), start values must be set for the values of parameters that are adjustable during operation of the hearing aid, affecting the volume setting or the sound for example. These start values are normally set when the hearing aid is programmed and stored in a non-volatile memory in the hearing aid. It is known that the hearing aid reverts to these start values each time it is turned on or switches operating mode. In addition, it is possible for the values set most recently prior to turning off or switching to a different operating mode to be stored as new start values which are then set automatically again when the hearing aid is turned on again or is switched to the operating mode in question again.

The underlying concept of the invention is based on the fact that when the hearing aid is turned on or when the hearing aid is switched to a particular operating mode, neither the value most recently valid for the parameter prior to turning off or switching to a different operating mode nor the parameter value transferred to the hearing aid at the beginning of programming is set. Rather, from the changes to the value of the parameter taking place during operation of the hearing aid a new start value is ascertained and stored, which value is then set automatically after turning on or switching mode.

This has the advantage that an automatic fine customization of the hearing aid takes place over time. The start values for the parameter in question when turning on or switching mode come ever closer to the habits, likes and preferred hearing environments of the user. For example, values which result from settings which the user makes during operation, an increase in volume for example, are not adopted directly as new "start values". Rather, further "parameters" such as the magnitude of the change made in order to get from the old setting to the new setting, the period of time for which the new setting is retained, or the frequency with which the parameter in question is changed, are also taken into consideration when determining a new start value for the parameter in question.

The values of the determined parameters are advantageously placed in a non-volatile memory which preserves the stored values even in the case of an interruption to the power supply, when the hearing aid has been turned off for example. The memory is preferably implemented as an EEPROM. In this situation, either the current start values of the parameters can be placed in the memory immediately after any change, or alternatively the hearing aid can, after actuating a control element to turn off the hearing aid, also first be transferred to a turn-off mode in which the current values are written to the memory in question before the power supply is interrupted.

With regard to a preferred embodiment of the invention, through programming the hearing aid in question it is possible to define for which of the parameters that can be set by the hearing aid wearer or automatically the values set prior to turning off are to be valid once again after turning on again, for which parameters a default setting is chosen after turning on and for which parameters an automatic customization, described above, of the start value takes place. For example, with regard to a hearing aid according to the invention it is thus possible to define that after turning on this is always initially operated in hearing program number 1, whereby the value calculated as the current start value prior to turning off is however set automatically with regard to the volume setting.

A fine customization of start values for certain parameters according to the invention can take place both with regard to parameters which the user can change during operation by actuating control elements and also with regard to parameters which are changed automatically as a result of signal analyses by the hearing aid.

The calculation of a new start value for the parameter in question takes place in accordance with a predefined function, whereby there are many different possible approaches for this actual function. A linear averaging or a recursive averaging of the values set most recently for the parameter in question can thus be defined by the function, for example. According to this function new start values, which are referred to here as "memory values", are then generated for the parameter in question during operation of the hearing aid, whereby the memory value calculated most recently prior to turning off or switching mode is stored as a new start value in the hearing aid.

Input to the function for the determination of new memory values preferably also includes—in addition to the start value and the period of time for which the current value of the parameter is set—at least one previously set value for the parameter or at least one previously determined memory value.

By preference, a memory value and thus ultimately a new start value are determined by means of an averaging procedure. A recursive averaging procedure or a linear averaging procedure come into consideration, for example.

A new memory value is advantageously determined in each case at specified time intervals or after any change in the value of the parameter.

In addition, the current memory value is advantageously stored in the memory facility as a new start value at specified time intervals. The current memory value can however also be stored as a new start value for the current operating mode immediately prior to switching to a different operating mode or prior to turning off the hearing aid.

According to a preferred embodiment, for different operating modes it is possible for different values to be set for a parameter and for different start values to be stored.

It is also possible to combine a plurality of different operating modes to form an operating mode class and to store different start values for different operating mode classes.

A certain value range is advantageously defined for the value of the parameter and the value range for the new start value is restricted to a value range which is smaller than the value range defined for the value of the parameter. In this situation, it is possible to define different value ranges for the start value of a parameter for different operating modes.

BRIEF DESCRIPTION OF THE DRAWINGS

The invention will be described in detail in the following with reference to an embodiment. In the drawings.

DETAILED DESCRIPTION OF THE INVENTION

Figure 1:
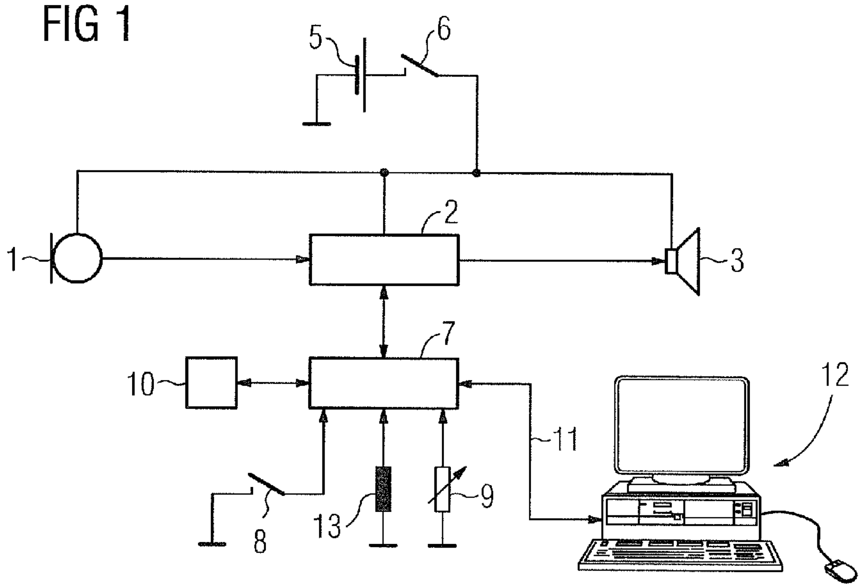
FIG. 1 shows a block diagram of a hearing aid according to the invention.

With regard to the hearing aid according to FIG. 1, a microphone 1 is provided for receiving an acoustic input signal and converting the acoustic input signal into an electrical input signal. The electrical input signal is fed to a signal processing unit 2 for further processing and frequency-dependent amplification. The further processed and amplified signal is finally converted by means of an earpiece 3 into an acoustic signal and delivered to the ear of a hearing aid wearer. The power supply for the hearing aid is provided by a battery 5 which is connected by way of an on/off switch 6 to the different electronic hearing aid components.

The signal processing in the signal processing unit 2 of the hearing aid can be customized by means of a control unit 7 to different hearing environments and hearing aid wearer preferences. In this situation, the parameters affecting signal processing can also be determined and set automatically by the control unit 7, for example as a result of analyzing the present hearing situation. In addition, the parameters affecting signal processing can also be set manually through actuation of control elements by the hearing aid wearer. In the embodiment, a program selector switch 8 and also a digital volume control 9 are provided for this purpose. In addition, the hearing aid includes a coil 13, by means of which a wireless signal transmission is possible between the hearing aid and a further device, for example a remote control facility or a second hearing aid. As a result, the parameter in question can also be customized by a signal transmitted wirelessly to the hearing aid.

The hearing aid according to the embodiment also has an interface 11 to a PC 12, which can be used to program the hearing aid. During programming it is also possible to define at least with regard to certain of the parameters that can be set by the user or automatically by the hearing aid whether a value that is valid before turning off also continues to be valid immediately after turning on or whether a standard value should be set for this purpose.

With regard to the hearing aid according to the embodiment, it is possible to specify by means of programming whether, after turning on, a predefined hearing program and also a predefined volume setting (default setting) are activated or whether the hearing program or the volume setting that was set before turning off is set, or whether a continuous calculation of a new start value should take place. At least in the latterly mentioned case, the value currently determined as the new start value (memory value) for the volume setting is placed in a non-volatile memory 10, for example. The latter preserves the values stored in it even if the power supply for the hearing aid is interrupted by opening the switch 6. When the hearing aid is turned on by closing the switch 6, the values stored previously in the non-volatile memory 10 are then read out and transferred to the control unit 7 which then uses the memory value determined most recently before turning off as the new start value to control the signal processing in the signal processing unit 2 with respect to the volume setting. The user does not therefore need to search again for the settings which he has found to be agreeable for himself prior to turning off. The hearing aid sets these automatically.

Figure 2:
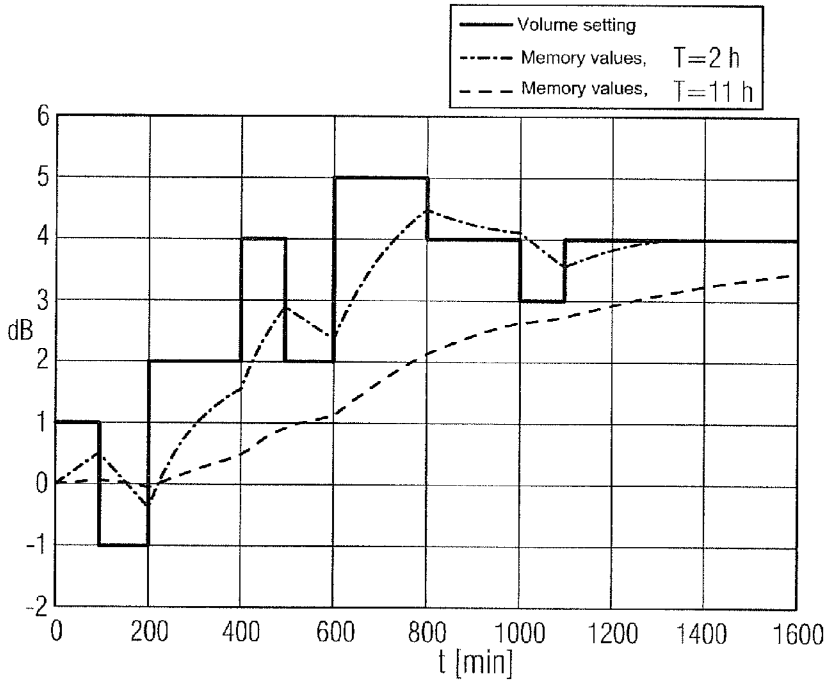
FIG. 2 shows the characteristics over time of new start values for the volume setting.

FIG. 2 shows the characteristics of new start values (memory values) over time for the volume setting. In this situation, the volume setting is changed abruptly by the user. The calculation of new memory values takes place in the embodiment by means of an exponential averaging algorithm, whereby the result of the calculation is illustrated for two different time constants.

The value for the volume setting currently valid prior to turning off or switching to a different hearing program is placed in the non-volatile memory as the new start value and is read out from the memory and set as the new start value when turning the hearing aid on again or when re-setting the hearing program in question.

The invention claimed is:

1. A method for operating a hearing aid, comprising:
setting a start value for a parameter of the hearing aid after a status change of the hearing aid occurs;
generating a current value for the parameter by changing the start value;
determining a memory value for the parameter based on the start value, the current value, and a period of time the current value is set;
storing the memory value in a memory unit of the hearing aid; and
setting the new start value for the parameter using the memory value after the status change of the hearing aid occurs again,
wherein a value range of the parameter is defined and a value range for the new start value of the parameter is defined within the value range of the parameter,
wherein a plurality of different value ranges for the new start value of the parameter are defined within the value range of the parameter for a plurality of different operating modes.

2. The method as claimed in claim 1, wherein the status change of the hearing aid comprises turning on the hearing aid or switching the hearing aid from a first operating mode to a second operating mode.

3. The method as claimed in claim 1, wherein the memory value is automatically determined and the start value and the new start value are automatically set.

4. The method as claimed in claim 1, wherein the current value is manually changed by a user of the hearing aid or automatically changed by a signal analysis and control unit of the hearing aid.

5. The method as claimed in claim 1, wherein a previously set value for the parameter prior to the current value or a previously determined memory value for the parameter prior to the current value is included in the determination of the memory value.

6. The method as claimed in claim 1, wherein the memory value is determined by an averaging method.

7. The method as claimed in claim 6, wherein the averaging method is selected from the group consisting of: a linear averaging method, a recursive averaging method, and an exponential averaging method.

8. The method as claimed in claim 1, wherein the memory value is determined at a specified time interval or after a value of the parameter has been changed.

9. The method as claimed in claim 1, wherein the memory value is stored in the memory unit as the new start value at a specified time interval or before the hearing aid switching to a different operating mode or before the hearing aid turning off.

10. The method as claimed in claim 1, wherein a set of different memory values are determined and stored as a set of new start values for a set of different operating modes of the hearing aid.

11. The method as claimed in claim 10, wherein the set of different operating modes are combined to an operating mode class.

12. The method as claimed in claim 11, wherein a plurality of different sets of operating modes are combined to a plurality of different operating mode classes and a plurality of different sets of new start values are determined and stored for the different mode classes.

13. The method as claimed in claim 1, wherein the parameter comprises a volume setting.

14. A hearing aid, comprising:

an input converter that receives an input signal and converts the input signal into an electrical input signal;

a signal processing unit that processes and amplifies the electrical input signal;

an output converter that converts the processed and amplified electrical input signal into an acoustic output signal;

a control unit that automatically sets a start value for a parameter of the hearing aid after a status change of the hearing aid occurs;

an operating unit that changes the start value of the parameter to a current value;

a calculation unit that automatically determines a memory value based on the start value, the current value, and a period of time the current value is set; and a memory unit that stores the memory value as a new start value if the status change of the hearing aid occurs again, wherein a value range of the parameter is defined and a value range for the new start value of the parameter is defined within the value range of the parameter, wherein a plurality of different value ranges for the new start value of the parameter are defined within the value range of the parameter for a plurality of different operating modes.

15. The hearing aid as claimed in claim 14, wherein the status change of the hearing aid comprises turning on the hearing aid or switching the hearing aid from a first operating mode to a second operating mode.

16. The hearing aid as claimed in claim 14, wherein the memory unit is a non-volatile memory unit, and wherein the non-volatile memory unit is an EEPROM.

17. The hearing aid as claimed in claim 14, wherein a program is installed in the hearing aid to define whether the memory value or a default setting of the parameter is set as the new start value for the parameter after the status change of the hearing aid occurs again.

18. The hearing aid as claimed in claim 14, wherein the hearing aid is worn on or in an ear of a user.

* * * * *